United States Patent [19]

Möller et al.

[11] 4,045,571
[45] Aug. 30, 1977

[54] PYRAZOL-5-ONES

[75] Inventors: Eike Möller; Karl Meng, both of Wuppertal; Egbert Wehinger, Neviges; Harald Horstmann, Wuppertal, all of Germany

[73] Assignee: Bayer Aktiengesellschaft, Germany

[21] Appl. No.: 633,601

[22] Filed: Nov. 20, 1975

Related U.S. Application Data

[62] Division of Ser. No. 459,408, April 9, 1974.

[30] Foreign Application Priority Data

Apr. 17, 1973 Germany .................. 2319278

[51] Int. Cl.$^2$ ........................................ A61K 31/415
[52] U.S. Cl. ................................................ 424/273 P
[58] Field of Search ................... 424/273; 260/310 A

[56] References Cited

U.S. PATENT DOCUMENTS

| | | | |
|---|---|---|---|
| 2,376,380 | 5/1945 | Porter et al. | 260/310 |
| 2,476,986 | 7/1949 | Martin | 260/310 |
| 2,476,987 | 7/1949 | Martin | 260/310 |
| 2,511,231 | 6/1950 | Weissberger et al. | 95/6 |
| 2,600,788 | 6/1952 | Loria et al. | 95/6 |
| 2,619,419 | 11/1952 | Jennen | 95/6 |
| 2,672,417 | 3/1954 | Jennen | 95/6 |
| 2,681,915 | 6/1954 | Gysin et al. | 260/310 |
| 2,848,446 | 8/1958 | Moderni | 260/147 |
| 3,014,916 | 12/1961 | Wright | 260/310 |
| 3,113,949 | 12/1963 | Bicking | 260/310 |
| 3,153,654 | 10/1964 | Ficken | 260/310 |
| 3,190,888 | 6/1965 | Wolf et al. | 424/273 |
| 3,558,319 | 1/1971 | Hamaoka et al. | 96/100 |
| 3,563,745 | 2/1971 | Eynde et al. | 96/56.5 |
| 3,615,502 | 10/1971 | Yoshida | 96/56.5 |
| 3,615,506 | 10/1971 | Abbott | 96/56.5 |
| 3,632,818 | 1/1972 | Allais et al. | 260/310 A |
| 3,694,456 | 9/1972 | Noguchi et al. | 260/310 R |
| 3,719,764 | 3/1973 | Gerault et al. | 424/273 |
| 3,812,145 | 5/1974 | Sato et al. | 260/310 A |
| 3,823,156 | 7/1974 | Oku et al. | 260/310 A |
| 3,949,083 | 4/1976 | Moller et al. | 424/273 |

FOREIGN PATENT DOCUMENTS

| | | |
|---|---|---|
| 727,091 | 7/1969 | Belgium |
| 2,068,413 | 8/1971 | France |
| 2,230,792 | 1/1974 | Germany |
| 1,003,215 | 7/1957 | Germany |
| 2,230,675 | 1/1974 | Germany |
| 779,703 | 7/1957 | United Kingdom |
| 961,037 | 6/1964 | United Kingdom |
| 599,919 | 3/1948 | United Kingdom |
| 1,190,914 | 5/1970 | United Kingdom |

Primary Examiner—Donald B. Moyer
Attorney, Agent, or Firm—Jacobs & Jacobs

[57] ABSTRACT

Pharmaceutical compositions useful for effecting diuresis and saluresis and for treating hypertension in humans and animals are produced by combining a pyrazol-5-one of the formula:

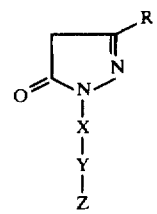

or a pharmaceutically acceptable nontoxic salt thereof wherein

R is hydrogen, lower alkyl or amino;

X is methylene, ethylene, methylene wherein 1 hydrogen atom is substituted by lower alkyl, or ethylene wherein 1 hydrogen atom is substituted by lower alkyl or 1 hydrogen atom on each of the two carbon atoms is substituted by lower alkyl;

Y is a direct bond, oxygen or sulphur, provided that when X is methylene wherein 1 hydrogen atom is substituted by alkyl of 1 to 4 carbon atoms, Y is a direct bond; Z is aryl of 6 to 10 carbon atoms unsubstituted or substituted by:

a. 1 to 2 of the same or different substituents selected from the group consisting of halogen, trifluoromethyl, alkyl of 1 to 4 carbon atoms, alkenyl of 2 to 4 carbon atoms, alkoxy of 1 to 4 carbon atoms, and alkenoxy of 2 to 4 carbon atoms; cycloalkenyl of 5, 6 or 7 carbon atoms;

c. lower alkylamino, dilower alkylamino, trifluoromethoxy, nitro, cyano, carbamoyl, lower alkylcarbamoyl, dilower alkylcarbamoyl, sulphamyl, lower alkylsulphamyl, dilower alkylsulphamyl, —SO$_n$—lower alkyl wherein $n$ is 0, 1 or 2, or said dialkylamino, carbamoyl, alkylcarbamoyl, dialkylcarbamoyl, sulphamyl, alkylsulphamyl, or dialkylsulphamyl, the nitrogen atom of which is a member of a 5-, 6- or 7-membered ring or said ring which additionally contains an oxygen atom;

d. lower alkylamino, dilower alkylamino, trifluoromethoxy, nitro, cyano, carbamoyl, lower alkylcarbamoyl, dilower alkylcarbamoyl, sulphamyl, lower alkylsulphamyl, dilower alkylsulphamyl, or —SO$_n$—lower alkyl wherein $n$ is 0, 1 or 2, and 1 or 2 substituents selected from the group consisting of alkyl of 1 to 4 carbon atoms, alkenyl of 2 to 4 carbon atoms, alkoxy of 1 to 4 carbon atoms, alkenoxy of 2 to 4 carbon atoms, halogen and trifluoromethyl; or e. a fused, saturated or unsaturated 5-, 6- or 7-membered ring or said ring additionally containing 1 or 2 oxygen or sulphur atoms, in combination with a pharmaceutically acceptable nontoxic inert diluent or carrier.

The compositions are preferably administered orally or parenterally and in the latter case, sterile or isotonic aqueous solutions are preferred.

42 Claims, No Drawings

PYRAZOL-5-ONES

CROSS-REFERENCE

This is a division of Ser. No. 459,408 filed Apr. 9, 1974.

The present invention relates to pharmaceutical compositions which are useful for effecting diuresis and saluresis in humans and animals and for treating hypertension in humans and animals. These compositions are characterized by the use of pyrazol-5-ones or pharmaceutically acceptable nontoxic salts thereof as the active agent.

3-Aminopyrazolones have been used as color couplers for color photography (A. Weissberger et al. J. Amer. Chem. Soc. 64, 2133 (1942), and as intermediates for the preparation of color couplers (British Pat. No. 599,919; U.S. Pat. Nos. 2,367,523; 2,376,380, 2,511,231, 2,600,788, 2,619,419, and 2,672,417).

Pyrazol-5-one derivatives are used as antipyretics, analgesics and antiphlogistics (of G. Ehrhart and H. Ruschig, "Arzneimittel," Vol. 1, p. 148 (1972)).

However, no diuretic, saluretic or antihypertensive activity is known for pyrazol-5-one derivatives.

It has now been discovered that pharmaceutical compositions can be prepared for use as diuretics, saluretics and antihypertensives by combining a pyrazol-5-one or pharmaceutically acceptable nontoxic salt thereof as hereinafter defined with a pharmaceutically, acceptable nontoxic inert diluent or carrier.

The present invention also comprises administering to humans or animals in need of diuretic, saluretic or antihypertensive therapy, pyrazol-5-ones or pharmaceutically acceptable nontoxic salts thereof as hereinafter defined.

More particularly, the present invention comprises a pharmaceutical composition which comprises a diuretic, saluretic or antihypertensive amount of a pyrazol-5-one of the formula:

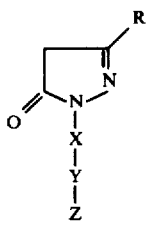

I or a pharmaceutically acceptable nontoxic salt thereof wherein

R is hydrogen, lower alkyl especially alkyl of 1 to 4 carbon atoms, or amino;

X is methylene, ethylene, methylene wherein 1 hydrogen atom is substituted by lower alkyl, or ethylene wherein 1 hydrogen atom is substituted by lower alkyl or 1 hydrogen atom on each of the two carbon atoms is substituted by lower alkyl;

Y is a direct bond, oxygen or sulphur, provided that when X is methylene wherein 1 hydrogen atom is substituted by alkyl of 1 to 4 carbon atoms, Y is a direct bond; and Z is aryl especially aryl of 6 to 10 carbon atoms unsubstituted or substituted by:
a. 1 or 2 of the same or different substitutents selected from the group consisting of halogen, trifluoromethyl, lower alkyl especially alkyl of 1 to 4 carbon atoms, lower alkenyl especially alkenyl of 2 to 4 carbon atoms, lower alkoxy especially alkoxy of 1 to 4 carbon atoms, and lower alkenoxy especially alkenoxy of 2 to 4 carbon atoms;
b. cycloalkyl of 5, 6 or 7 carbon atoms, or cycloakenyl of 5, 6 or 7 carbon atoms;
c. lower alkylamino, dilower alkylamino, trifluoromethoxy, nitro, cyano, carbamoyl, lower alkylcarbamoyl, dilower alkylcarbamoyl, sulphamyl, lower alkylsulphamyl, dilower alkylsulphamyl, —$SO_n$-lower alkyl wherein n is 0, 1 or 2, or said dialkylamino, carbamoyl, alkylcarbamoyl, dialkylcarbamoyl, sulphamyl, alkylsulphamyl, or dialkylsulphamyl, the nitrogen atom of which is a member of a 5-, 6- or 7-membered ring or said ring which additionally contains an oxygen atom;
d. lower alkylamino, dilower alkylamino, trifluoromethoxy, nitro, cyano, carbamoyl, lower alkylcarbamoyl, dilower alkylcarbamoyl, sulphamyl, lower alkylsulphamyl, dilower alkylsulphamyl, —$SO_n$-lower alkyl wherein n is 0, 1 or 2, or said dialkylamino, carbamoyl, alkylcarbamoyl, dialkylcarbamoyl, sulphamyl, alkylsulphamyl, or dialkylsulphamyl, the nitrogen atom of which is a member of a 5-, 6- or 7-membered ring or said ring which additionally contains an oxygen atom, and 1 or 2 substituents selected from the group consisting of lower alkyl especially alkyl of 1 to 4 carbon atoms, lower alkenyl especially alkenyl of 2 to 4 carbon atoms, lower alkoxy especially alkoxy of 1 to 4 carbon atoms, lower alkenoxy especially alkenoxy of 2 to 4 carbon atoms, halogen and trifluoromethyl; or
e. a fused, saturated or unsaturated 5-, 6- or 7-membered ring or said ring additionally containing 1 or 2 oxygen or sulphur atoms, in combination with a pharmaceutically acceptable nontoxic inert diluent or carrier.

As used herein the expression "compounds of the present invention" means both the pyrazol-5-ones of formula I above and their pharmaceutically acceptable nontoxic salts.

The phrase "lower alkyl," "lower alkenyl," "lower alkoxy" and "lower alkenoxy" include both straight and branched chain moieties.

The compounds according to the present invention exist not only in the form shown in formula I but also in the following tautomeric forms:

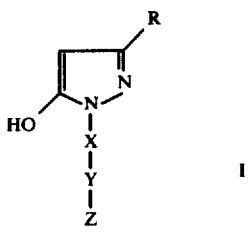

(a)

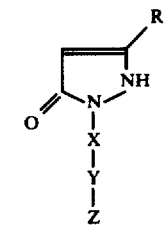

(b)

Specifically, the 3-aminopyrazol-5-ones may, additionally, occur in the forms I (c) and I (d):

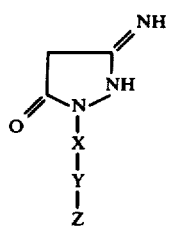
(c)

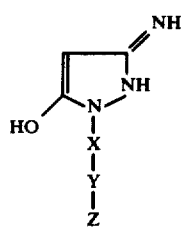
(d)

I

The present invention includes the use of the pyrazol-5-ones and their pharmaceutically acceptable nontoxic salts in any of the tautomeric forms in which they exist.

In addition, when X in formula I contains an asymmetric carbon atom, the compound exists as a racemate and can be resolved into its antipodes. The compositions of the present invention must include the pyrazol-5-ones and pharmaceutically acceptable nontoxic salts thereof in the form of the optical isomers as well as the racemates.

According to one embodiment of the present invention:

R is hydrogen, alkyl of 1 to 4 carbon atoms, or amino; and

Z is phenyl, or naphthyl unsubstituted or substituted by a. 1 or 2 of the same of different substituents selected from the group consisting of halogen, trifluoromethyl, alkyl of 1 to 4 carbon atoms, alkenyl of 2 to 4 carbon atoms, alkoxy of 1 to 4 carbon atoms, and alkenoxy of 2 to 4 carbon atoms;

b. alkylamino of 1 to 4 carbon atoms, dialkylamino of 1 to 4 carbon atoms in each alkyl moiety, trifluoromethoxy, nitro, cyano, carbamoyl, alkylcarbamoyl of 1 to 4 carbon atoms in the alkyl moiety, dialkylcarbamoyl of 1 to 4 carbon atoms in each alkyl moiety, sulphamyl, alkylsulphamyl of 1 to 4 carbon atoms, dialkylsulphamyl of 1 to 4 carbon atoms in each alkyl moiety, or $-SO_n-$alkyl of 1 to 4 carbon atoms wherein $n$ is 0, 1 or 1;

c. alkylamino of 1 to 4 carbon atoms, dialkylamino of 1 to 4 carbon atoms in each alkyl moiety, trifluoromethoxy, nitro, cyano, carbamoyl, alkylcarbamoyl of 1 to 4 carbon atoms in the alkyl moiety, dialkylcarbamoyl of 1 to 4 carbon atoms in each alkyl moiety, sulphamyl, alkylsulphamyl of 1 to 4 carbon atoms, dialkylsulphamyl of 1 to 4 carbon atoms in each alkyl moiety, $SO_n-$alkyl of 1 to 4 carbon atoms wherein $n$ is 0, 1 or 2, and 1 or 2 substituents selected from the group consisting of alkyl of 1 to 4 carbon atoms, alkenyl of 2 to 4 carbon atoms, alkoxy of 1 to 4 carbon atoms, alkenoxy of 2 to 4 carbon atoms, halogen and trifluoromethyl; or d. a fused, saturated or unsaturated 5, 6- or 7-membered ring or said ring additionally containing 1 or 2 oxygen or sulphur atoms.

According to another embodiment of the present invention:

R is hydrogen, alkyl of 1 to 4 carbon atoms, or amino;

X is methylene 1 hydrogen atom of which is substituted by alkyl of 1 to 4 carbon atoms, or ethylene 1 hydrogen atom of which is substituted by methyl or ethyl or 1 hydrogen atom of each of the two carbon atoms of which is substituted by methyl or ethyl;

Z is phenyl, or naphthyl substituted by:

a. 1 or 2 of the same or different substituents selected from the group consisting of alkyl of 1 to 8 carbon atoms, and alkenyl of 1 to 8 carbon atoms;

b. 1 or 2 of the same or different substituents selected from the group consisting of alkoxy of 1 to 6 carbon atoms, and alkenoxy of 2 to 6 carbon atoms;

c. cycloalkyl of 5, 6 or 7 carbon atoms, or cycloalkenyl of 5, 6, or 7 carbon atoms;

d. 1 or 2 trifluoromethyl moieties;

e. trifluoromethoxy, nitro or cyano;

f. dialkylamino of 1 to 4 carbon atoms in each alkyl moiety, carbamoyl, alkylcarbamoyl of 1 to 4 carbon atoms in the alkyl moiety, dialkylcarbamoyl of 1 to 4 carbon atoms in each alkyl moiety, sulphmyl, alkylsulphamoyl of 1 to 4 carbon atoms in the alkyl moiety, dialkylsulphamoyl of 1 to 4 carbon atoms in each alkyl moiety, or said alkylamino, carbamoyl, alkylcarbamoyl, dialkylcarbamoyl, sulphamyl, alkylsulphamyl or dialkylsulphamyl, the nitrogen atom of which is a member of a 5-, 6- or 7-membered ring or said ring additionally containing an oxygen atom;

g. $-SO_n-$alkyl of 1 to 4 carbon atoms wherein $n$ is 0, 1 or 2; or h. a fused, saturated or unsaturated 5-, 6- or 7-membered ring or said ring which also contains 1 or 2 oxygen atoms or 1 sulphur atom.

According to another embodiment of the present invention:

R is hydrogen, alkyl of 1 to 4 carbon atoms, or amino;

X is methylene 1 hydrogen atom of which is substituted by alkyl of 1 to 4 carbon atoms, or ethylene 1 hydrogen atom of which is substituted by methyl or ethyl or 1 hydrogen atom of each of the two carbon atoms of which is substituted by methyl or ethyl;

Z is phenyl, naphthyl, or phenyl substituted by:

a. 1 or 2 of the same or different substitutents selected from the group consisting of alkyl of 1 to 4 carbon atoms, and alkenyl of 2 to 4 carbon atoms;

b. 1 or 2 of the same or different substituents selected from the group consisting of alkoxy of 1 to 6 carbon atoms, and alkenoxy of 2 to 6 carbon atoms;

c. cycloalkyl of 5, 6 or 7 carbon atoms, or cycloalkenyl of 5, 6 or 7 carbon atoms;

d. 1 or 2 trifluoromethyl moieties;

e. trifluoromethoxy, nitro or cyano;

f. dialkylamino of 1 to 4 carbon atoms in each alkyl moiety, carbamoyl, alkylcarbamoyl of 1 to 4 carbon atoms in the alkyl moiety, dialkylcarbamoyl of 1 to 4 carbon atoms in each alkyl moiety, sulphamyl, alkylsulphamyl of 1 to 4 carbon atoms in the alkyl moiety, dialkylsulphamyl of 1 to 4 carbon atoms in each alkyl moiety, or said alkylamino, carbamoyl, alkylcarbamoyl, dialkylcarbamoyl, sulphamyl, alkylsulphamyl or dialkylsulphamyl, the nitrogen atom of which is a member of a 5-, 6- or 7-membered ring or said ring additionally containing an oxygen atom;

g. $-SO_n-$alkyl of 1 to 4 carbon atoms wherein $n$ is 0 or 2; or h. a fused, saturated or unsaturated 5-, 6- or 7-membered ring or said ring which also contains 1 or 2 oxygen atoms or 1 sulphur atom.

According to another embodiment of the present invention:

R is hydrogen, alkyl of 1 to 4 carbon atoms, or amino;

X is methylene, methylene 1 hydrogen atom of which is substituted by alkyl of 1 to 3 carbon atoms, ethylene, ethylene 1 hydrogen atom of which is substituted by alkyl of 1 to 3 carbon atoms, or ethylene wherein 1 hydrogen atom of each of the two carbon atoms is substituted by alkyl of 1 to 3 carbon atoms; and Z is phenyl, naphthyl, or phenyl substituted by:
a. cyclohexyl or phenyl;
b. 1 or 2 of the same or different substituents selected from the group consisting of fluorine, chlorine, bromine, iodine, alkyl of 1 to 4 carbon atoms, alkoxy of 1 to 4 carbon atoms, trifluoromethyl, trifluoromethoxy, nitro, cyano, dialkylamino of 1 or 2 carbon atoms in each alkyl moiety, and sulphamyl; or
c. a trimethylene or tetramethylene moiety which forms a 5- or 6-membered ring together with two carbon atoms of the phenyl ring.

According to another embodiment of the present invention:

R is hydrogen, methyl, ethyl, n-propyl, isopropyl, or n-butyl;

X is methylene, methylene 1 hydrogen atom of which is substituted by methyl, ethyl, or n-propyl, ethylene, ethylene 1 hydrogen atom of which is substituted by methyl, ethyl or n-propyl, or ethylene wherein 1 hydrogen atom on each of the two carbon atoms is substituted by methyl;

Y is a direct bond, oxygen or sulphur, provided that when X is methylene, 1 hydrogen atom of which is substituted by methyl, ethyl, or n-propyl, Y is a direct bond; and Z is phenyl, naphthyl, or phenyl substituted by alkyl of 1 to 4 carbon atoms, alkoxy of 1 or 2 carbon atoms, fluorine, chlorine, bromine, iodine, trifluoromethyl, trifluoromethoxy, nitro, cyano, cyclohexyl, phenyl, dimethylamino, sulphamyl, dichlorine, chlorine and bromine, chlorine and fluorine, chlorine and methyl, chlorine and trifluoromethyl, chlorine and sulphamyl, chlorine and trifluoromethyl, fluorine and methyl, trifluoromethyl and methyl, dimethyl, or a trimethylene or tetramethylene moiety which forms a 5- or 6-membered ring together with two carbon atoms of the phenyl ring.

According to another embodiment of the present invention:

R is hydrogen, methyl, ethyl, or amino;

X is methylene 1 hydrogen atom of which is substituted by methyl, ethyl, or n-propyl, ethylene, or ethylene 1 hydrogen atom of which is substituted by methyl;

Y is a direct bond, oxygen or sulphur, provided that when X is methylene, 1 hydrogen atom of which is substituted by methyl, etyl, or n-propyl, Y is a direct bond; and Z is phenyl, naphthyl, or phenyl substituted by 1 or 2 of the same or different substitutents selected from the group consisting of fluorine, chlorine, bromine, methyl, ethyl, and trifluoromethyl.

According to another embodiment of the present invention:

R is methyl, ethyl, or amino;

X is methylene 1 hydrogen atom of which is substituted by methyl, ethyl, or n-propyl, ethylene, or ethylene 1 hydrogen atom of which is substituted by methyl;

Y is a direct bond, oxygen or sulphur, provided that when X is methylene 1 hydrogen atom of which is substituted by methyl, ethyl, or n-propyl, y is a direct bond; and Z is phenyl, naphthyl, or phenyl substituted by fluorine, chlorine, bromine, methyl, trifluoromethyl, dichlorine, dimethyl, chlorine and methyl, or methyl and ethyl.

The pyrazol-5-ones of the present invention may be prepared by reacting a hydrazine of the formula II:

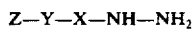

wherein

X, Y and Z are as above defined, with an acetic acid derivative of the formula III:

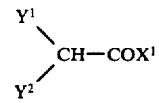

wherein $X^1$ is hydroxy, lower alkoxy, aralkoxy preferably comprising a monoaryl moiety and a lower alkoxy moiety, amino or lower alkylamino;

$Y^1$ is hydrogen, and $Y^2$ is cyano or a moiety of the formula:

wherein $Y^3$ is hydrogen or straight or branched chain alkyl of 1 to 4 carbon atoms; or $Y^1$ and $Y^2$ together form the moiety:

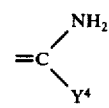

wherein $Y^4$ is lower alkoxy, aryloxy preferably monoaryloxy, aralkoxy preferably comprising a monoaryl moiety and a lower alkoxy moiety, lower alkylmercapto, aralkylmercapto preferably comprising a monoaryl moiety in the lower alkyl moiety, or amino, either in the presence or the absence of an inert solvent and of a basic or acetic catalyst such as an alkali metal hydroxide, carbonate, halogen hydracid, sulphuric acid or a sulphonic acid, at a temperature between 10° and 200° C.

The pyrazol-5-ones of formula I and their pharmaceutically acceptable nontoxic salts may be interconverted according to techniques which are per se known in the art.

The racemates according to the present invention may be resolved into their optical antipodes:

1. According to methods known in the literature (see, e.g. Houben Weyl's "Methoden der Organischen Chemie" IV/2, page 509 ff) by interaction of a racemic compound used according to the invention with a chiral medium, preferably by reaction of the said compound with a derivative of an optically active acid (e.g. camphorsulphonic acid, bromocamphorsulphonic acid or quinic acid) or of an optically active base (e.g. brucine, morphine or strychnine) to give a mixture of diastereoisomeric reaction products. These products can, with the aid of physicochemical methods (e.g. fractionation) be separated and prepared pure, and substantially again resolved into their components.

or

2. By reaction of the optically pure hydrazine of the formula II (which can be prepared by methods known from the literature) with an acetic acid derivative of the formula III, e.g.

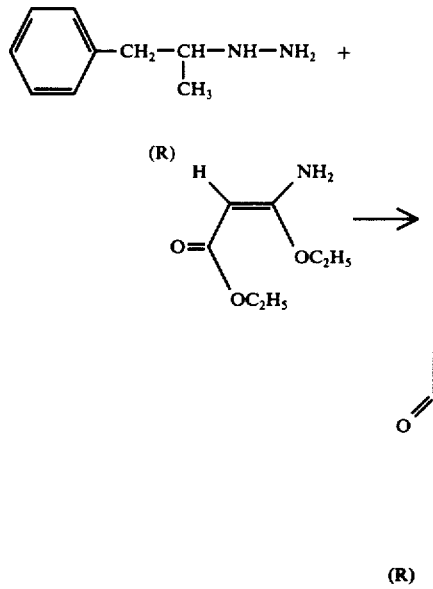

The following compounds are representative of those of the present invention:

1-(α-methylbenzyl)-pyrazol-5-one,
1-(α-methyl-3,4-dichlorobenzyl)-pyrazol-5-one,
1-(β-phenoxyethyl)-pyrazol-5-one,
1-(β-(3-methylphenylmercapto)-ethyl)-pyrazol-5-one,
1-(β-phenethyl)-pyrazol-5-one,
3-amino-1-(α-methyl-3-chlorobenzyl)-pyrazol-5-one,
3-amino-1-(α-methyl-3-bromobenzyl)-pyrazol-5-one,
3-amino-1-(α-methyl-3-fluorobenzyl)-pyrazol-5-one,
3-amino-1-(α-methyl-4-fluorobenzyl)-pyrazol-5-one,
3-amino-1-(α-methyl-4-iodobenzyl)-pyrazol-5-one,
3-amino-1-(α-methyl-4-trifluoromethylbenzyl)-pyrazol-5-one,
3-amino-1-(α-methyl-4-trifluoromethoxybenzyl)-pyrazol-5-one,
3-amino-1-(α-methyl-3-trifluoromethyl-4-methylbenzyl)-pyrazol-5-one,
3-amino-1-(α-methyl-3-chloro-4-bromobenzyl)-pyrazol-5-one,
3-amino-1-(α-(naphthyl-(2)-ethyl)-pyrazol-5-one,
3-amino-1-(α-ethyl-4-nitrobenzyl)-pyrazol-5-one,
3-amino-1-(α-ethyl-4-cyanobenzyl)-pyrazol-5-one,
3-amino-1-(α-n-propyl-2-chloro-4-fluorobenzyl)-pyrazol-5-one,
3-amino-1-(β-(2-methylphenoxy)-ethyl)-pyrazol-5-one,
3-amino-1-(β-(2-chlorophenoxy)-ethyl)-pyrazol-5-one,
3-amino-1-(α-methyl-β-phenoxyethyl)-pyrazol-5-one,
3-amino-1-(α-methyl-β-(3-chloro-4-methylphenoxy)-ethyl)pyrazol-5-one,
3-amino-1-(β-methyl-β-(4-cyclohexylphenoxy)-ethyl)-pyrazol-5-one,
3-amino-1-(β-(2-nitrophenoxy)-ethyl)-pyrazol-5-one,
3-amino-1-(β-ethyl-β-(4-isopropylphenoxy)-ethyl)-pyrazol-5-one,
3-amino-1-(β-methyl-β-(4-methylphenylmercapto)-ethyl)pyrazol-5-one,
3-amino-1-(β-(naphthyl-(2)-mercapto)-ethyl)-pyrazol-5-one,
3-amino-1-(β3,4-trimethylenephenyl)-ethyl)-pyrazol-5-one,
3-amino-1-(β4-chlorophenyl)-ethyl)-pyrazol-5-one,
3-amino-1-(α,β-dimethyl-β-phenethyl)-pyrazol-5-one,
3-amino-1-(β-methyl-β-(3-chloro-4-methylphenyl)-ethyl)-pyrazol-5-one,
3-amino-1-(α-ethyl-β-phenethyl)-pyrazol-5-one,
3-amino-1-(α-methyl-4-sulphonamidobenzyl)-pyrazol-5-one,
3-amino-1-(α-methyl-4-chloro-3-sulphonamidobenzyl)-pyrazol-5-one,
3-methyl-1-(α-methyl-4-butylbenzyl)-pyrazol-5-one,
3-methyl-1-(α-methyl-3-trifluoromethyl-4-chlorobenzylpyrazol-5-one,
3-methyl-1-(α-methyl-4-sulphonamidobenzyl)-pyrazol-5-one,
3-methyl-4-dimethylaminobenzyl)-pyrazol-5-one,
3-methyl-1-(α-methyl-3,4-tetramethylenebenzyl)-pyrazol-5-one,
3-methyl-1-(α-methyl-3-chlorobenzyl)-pyrazol-5-one,
3-methyl-1-(α-methyl-2-chlorobenzyl)-pyrazol-5-one,
3-methyl-1-(α-methyl-3,5-dichlorobenzyl)-pyrazol-5-one,
3-methyl-1-(α-methyl-4-fluorobenzyl)-pyrazol-5-one,
3-methyl-1-(α-methyl-4-chloro-3-bromobenzyl)-pyrazol-5-one,
3-methyl-1-(α-methyl-4-fluoro-3-chlorobenzyl)-pyrazol-5-one,
3-methyl-1-(α-methyl-3-methylbenzyl)-pyrazol-5-one,
3-methyl-1-(α-methyl-4-ethylbenzyl)-pyrazol-5-one,
3-methyl-1-(α-methyl-4-chloro-3-methylbenzyl)-pyrazol-5-one,
3-methyl-1-(α-methyl-4-fluoro-3-methylbenzyl)-pyrazol-5-one,
3-methyl-1-(α-methyl-3-methyl-5-chlorobenzyl)-pyrazol-5-one,
3-methyl-1-(α-methyl-3,5-dimethylbenzyl)-pyrazol-5-one,
3-methyl-1-(α-methyl-3-chloro-4-trifluoromethylbenzyl)-pyrazol-5-one,
3-methyl-1-(α-methyl-3-methyl-4-trifluoromethylbenzyl)-pyrazol-5-one,
3-methyl-1-(α-methyl-3-methoxybenzyl)-pyrazol-5-one,
3-methyl-1-(α-methyl-4-ethoxybenzyl)-pyrazol-5-one,
3-methyl-1-(α-methyl-3-ethylbenzyl)-pyrazol-5-one,
3-methyl-1-(β-methyl-β-phenoxyethyl)-pyrazol-5-one,
3-methyl-1-(β-ethyl-β-phenoxyethyl)-pyrazol-5-one,
3-methyl-1-(β-methyl-β-(3-chlorophenoxy)-ethyl)-pyrazol-5-one,
3-methyl-1-(β-methyl-β-(4-chlorophenoxy)-ethyl)-pyrazol-5-one, 3-methyl-1-(β-n-propyl-β-(3,4-dichlorophenoxy)-ethyl)-pyrazol-5-one,
3-methyl-1-(β-4-trifluoromethoxyphenoxy)-ethyl)-pyrazol-5-one,
3-methyl-1-(β-(4-dimethylaminophenoxy)-ethyl)-pyrazol-5-one,
3-methyl-1-(β-(4-iodophenoxy)-ethyl)-pyrazol-5-one,
3-methyl-1-(β-(3,4-dichlorophenoxy)-ethyl)-pyrazol-5-one,
3-methyl-1-(β-(3-chloro-4-methylphenoxy)-ethyl)-pyrazol-5-one,
3-methyl-1-(β-(naphthyl-(2)-mercapto)-ethyl)-pyrazol-5-one,
3-methyl-1-(β-methyl-β-(3-chlorophenylmercapto-ethyl-pyrazol-5-one,
3-methyl-1-(β-methyl-β-(4-chlorophenylmercapto)-ethyl)-pyrazol-5-one,
3-methyl-1-(β-methyl-β-(3,4-dichlorophenylmercapto)-ethyl)-pyrazol-5-one,
3-ethyl-1-(β-ethyl-β(4-phenylphenoxy)-ethyl)-pyrazol-5-one,
3-ethyl-1-(α-methyl-3-methyl-4-chlorobenzyl)-pyrazol-5-one,
3-ethyl-1-(α-methyl-3-chloro-4-methylbenzyl)-pyrazol-5-one,
3-ethyl-1-(α-methyl-3,4-dichlorobenzyl)-pyrazol-5-one,
3-ethyl-1-(α-methyl-4-trifluoromethoxybenzyl)-pyrazol-5-one,
3-ethyl-1-(α-methyl-4-methyl-3-trifluoromethylbenzyl)-pyrazol-5-one,
3-ethyl-1-(α-methyl-4-bromo-3-chlorobenzyl)-pyrazol-5-one,
3-ethyl-1-(β-phenylmercaptoethyl)-pyrazol-5-one,
3-ethyl-1-(α,β-dimethyl-β-phenethyl)-pyrazol-5-one,
3-isopropyl-1-(α-methyl-3,4-dichlorobenzyl)-pyrazol-5-one,
3-n-propyl-1-(β-phenoxyethyl)-pyrazol-5-one, and
3-n-butyl-1-(β-phenoxyethyl)-pyrazol-5-one.

The pharmaceutical compositions of the present invention contain a major or minor amount e.g. 99.5% to 0.1%, preferably 90% to 0.5% of at least one pyrazol-5-one as above defined in combination with a pharmaceutically acceptable nontoxic, inert diluent or carrier, the carrier comprising one or more solid, semi-solid or liquid diluent, filler and formulation adjuvant which is nontoxic, inert and pharmaceutically acceptable. Such pharmaceutical compositions re preferably in dosage unit form; i.e. physically discrete units containing a predetermined amount of the drug corresponding to a fraction or multiple of the dose which is calculated to produce the desired therapeutic response. The dosage units can contain one, two, three, four or more single doses or alternatively, one-half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the parenteral dosage will be from 0.01 to 50 mg/kg, preferably 0.1 to 10 mg/kg, of body weight per day, and the oral dosage will be from 0.1 to 500 mg/kg, preferably 0.5 to 100 mg/kg, of body weight per day. In some instances a sufficient therapeutic effect can be obtained at a lower dose while in others, a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl, cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected utilizing suppositories in which the compound is admixed with low melting water soluble or insoluble solids such as polyethylene glycol, cocoa butter, higher esters as for example myristyl palmitate, or mixtures thereof.

The preferred daily dose for parenteral administration is 0.5 mg to 5 g., especially 5 mg to 1 g., and for oral administration the preferred daily dose is 5 mg to 50 g., especially 25 mg to 10 g. of active ingredient.

While the routes of administration include oral, parenteral (i.e. intramuscular, intraperitoneal, and intravenous) and rectal, oral and parenteral are particularly preferred. For parenteral administration, it is preferred that the solutions and emulsions be sterile and, if appropriate, blood-isotonic.

Examples of oral and parenteral administrable compositions include the following:

a. Tablets 200 g of 3-amino-1-(α-methyl-4-chlorobenzyl)-pyrazol-5-one are ground to a powder and mixed with 300 g of lactose and 200 g of potato starch, and after being moistened with an aqueous gelatine solution the mixture is granulated through a sieve.

After drying, 60 g of talc and 5 g of sodium laurylsulphate are added. About 10,000 tablets each containing 20 mg of active compound are pressed from this mixture.

b. Ampoules of injectable solution for parenteral use 20 g of the sodium salt of 3-methyl-1-(α-methyl-3-chlorobenzyl)-pyrazol-5-one are dissolved in 1,000 ml of propylene glycol and the solution is made up to 5,000 ml with water.

This solution is filled under aseptic conditions into sterile ampoules each of 5 ml capacity and each containing 20 mg of active compound.

The compounds used according to the present invention cause, on oral or parenteral administration, a strong increase of excretion of water and salt and are therefore useful for the treatment of oedematous and hypertonic conditions and for flushing out toxic substances. In addition, the compounds can be used in the case of acute renal insufficiency.

To demonstrate the diuretic and saluretic effect of the compounds used according to the invention, 3-methyl-1-(α-methyl-3,4-dichlorobenzyl)-pyrazol-5-one, described in Example 5, was administered to dogs. The remaining compounds show comparable properties.

Diuresis test with dogs a. Method

Beagle bitches were given, at intervals of 30 minutes, using a probang, 1 ml/kg body weight of a solution containing 0.4% of NaCl and 0.2 of KCl. The test preparation, in 0.5 mk/kg of 0.1% strength tragacanth mucilage, was then administered orally and the change in electrolyte excretion in the urine was measured by comparison with control groups. The excretion in Val/kg could then be calculated from the volume of urine and the measured electrolyte concentration. Sodium and potassium were determined by flame photometry.

b. Results

The results are shown in Table 1. The renal excretion of sodium and water was considerably increased after oral administration of the test preparation. The effect was dependent on the dosage.

Table 1

| | Excretion in μ equivalents/kg/30 minutes (Na+ + K+) and in ml/kg/30 minutes (urine) | | | | | | | |
|---|---|---|---|---|---|---|---|---|
| | Minutes after administration | 1-30 | 31-60 | 61-90 | 91-120 | 121-150 | 151-180 | Total excretion after administration |
| control | urine | 1.1 | 1.3 | 1.3 | 1.4 | 1.4 | 0.7 | 7.2 |
| | Na+ | 68 | 79 | 45 | 57 | 51 | 36 | 336 |
| | K+ | 88 | 88 | 64 | 45 | 42 | 25 | 352 |
| 1 mg/kg | urine | 4.5 | 11.9 | 4.6 | 3.9 | 1.0 | 0.6 | 26.5 |
| administered | Na+ | 358 | 1238 | 535 | 428 | 64 | 14 | 2637 |
| orally | K+ | 170 | 259 | 165 | 212 | 102 | 67 | 975 |
| 3 mg/kg | urine | 10.0 | 16.1 | 9.8 | 5.0 | 2.5 | 2.0 | 45.4 |
| administered | Na+ | 969 | 1932 | 1251 | 622 | 283 | 218 | 5275 |
| orally | K+ | 216 | 259 | 216 | 152 | 119 | 103 | 1065 |

Action of 3-methyl-1-(α-methyl-3,4-dichlorobenzyl)-pyrazol-5-one on the renal excretion of electrolyte and urine in awake dogs, as a function of time, and total effect after 3 hours. (Mean values for groups of 4 animals).

The effect of other compounds representative of those of the present invention is set forth in Table 2.

Table 2

| Excretion in μ equivalents/kg/hour (Na+ + K+) and in ml/kg/hour (urine) | | | | |
|---|---|---|---|---|
| Control | | Dose | Na+ | K+ | urine |
| | | | 140 | 152 | 2.0 |
| | | 10 mg/kg administered orally | 395 | 297 | 3.4 |

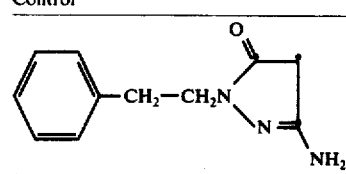

(Example 19)

Table 2-continued

| Control | Dose | Na+ 140 | K+ 152 | urine 2.0 |
|---|---|---|---|---|
| (Example 1a) phenyl-CH(CH₃)-N-pyrazolone (3-methyl) | 3 mg/kg administered orally | 472 | 185 | 6.5 |
|  | 10 mg/kg administered orally | 1050 | 330 | 14.7 |
| (Example 6) phenyl-O-CH₂-CH₂-N-pyrazolone (3-methyl) | 3 mg/kg administered orally | 1122 | 461 | 11.8 |
|  | 10 mg/kg administered orally | 2964 | 514 | 22.8 |
| (Example 24) phenyl-O-CH₂-CH₂-N-pyrazolone (3-NH₂) | 3 mg/kg administered orally | 1637 | 218 | 14.9 |
| (Example 15) phenyl-CH(CH₃)-N-pyrazolone (3-C₂H₅) | 3 mg/kg administered orally | 397 | 278 | 5.7 |
| (Example 9) phenyl-O-CH₂-CH(CH₃)-N-pyrazolone (3-methyl) | 3 mg/kg administered orally | 1693 | 283 | 13.6 |
| (Example 4) 4-Br-phenyl-CH(CH₃)-N-pyrazolone (3-methyl) | 3 mg/kg administered orally | 1106 | 334 | 8.7 |

The following non-limitative examples more particularly illustrate the present invention.

EXAMPLE 1

3-methyl-1-(α-n-propylbenzyl)-pyrazol-5-one

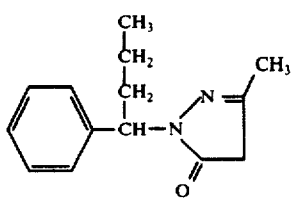

13 g of acetoacetic acid ethyl ester were dissolved in 20 ml of absolute ethanol. 16.4 g of α-n-propylbenzylhydrazine in a little absolute ethanol were slowly added to this solution under nitrogen. After the exothermic reaction had subsided, the mixture was heated for 2 hours under reflux.

On cooling, the crude product crystallized out and was purified by recrystallization from methanol.

Melting point: 125°-127° C
Yield: 15 g (65% of theory).

In a manner analogous to that described in Example 1, the compounds set forth in Table 3 may be similarly obtained.

Table 3

| Example No. | Structural formula | Recrystallization from | Yield | Melting point, °C |
|---|---|---|---|---|
| 1a | [phenyl-CH(CH₃)-N-pyrazolinone with CH₃] | Ethanol | 78% of theory | 167-169 |
| 2 | [phenyl-CH(C₂H₅)-N-pyrazolinone with CH₃] | Ethanol | 65% of theory | 158-160 |
| 3 | [H₃C-phenyl-CH(CH₃)-N-pyrazolinone with CH₃] | Methanol | 71% of theory | 144-146 |
| 4 | [Br-phenyl-CH(CH₃)-N-pyrazolinone with CH₃] | Dimethylformamide | 63% of theory | 150-152 |
| 4a | [F-phenyl-CH(CH₃)-N-pyrazolinone with CH₃] | Ethanol | 55% of theory | 140-142 |
| 5 | [Cl,Cl-phenyl-CH(CH₃)-N-pyrazolinone with CH₃] | Ethanol | 77.7% of theory | 143-145 |
| 6 | [phenyl-O-CH₂-CH₂-N-pyrazolinone with CH₃] | Ethanol | 83% of theory | 165-167 |
| 7 | [H₃C-phenyl-O-CH₂-CH₂-N-pyrazolinone with CH₃] | Ethanol | 60% of theory | 93-95 |
| 8 | [H₃C-phenyl-O-CH₂-CH₂-N-pyrazolinone with CH₃] | Methanol | 73% of theory | 135-137 |
| 9 | [phenyl-O-CH₂-CH(CH₃)-N-pyrazolinone with CH₃] | Methanol | 82% of theory | 133-135 |
| 10 | [Cl-phenyl-O-CH₂-CH(CH₃)-N-pyrazolinone with CH₃] | Methanol | 65% of theory | 130-132 |

Table 3-continued

| Example No. | Structural formula | Recrystallization from | Yield | Melting point, °C |
|---|---|---|---|---|
| 11 | 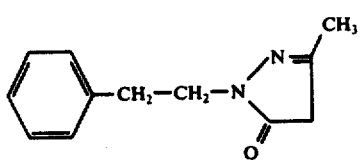 | Ethanol | 85% of theory | 83-85 |

Example 12

3-methyl-1-(β-phenethyl)-pyrazol-5-one

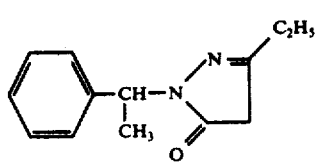

13.6 g (0.1 mol) of phenethylhydrazine were added under nitrogen to a solution of 13 g (0.1 mol) of acetoacetic acid ethyl ester in 20 ml of absolute dioxane; during the addition, the temperature rose to 62° C.

After completion of the addition, the reaction mixture was heated for 2 hours under reflux.

On cooling, the reaction product crystallized out. It was recrystallized from ethanol.

Melting point: 130°-132° C Yield: 13.3 g (66% of theory).

In a manner analogous to that described in Example 12, the compounds set forth in Table 4 may be similarly obtained.

EXAMPLE 16

3-ethyl-1-(β-phenoxymethyl)-pyrazol-5-one

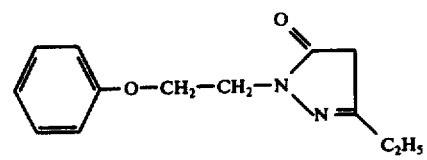

17.5 g (0.121 mol) of propionylacetoacetic acid ester were added under nitrogen to a solution of 18.4 g (0.121 mol) of phenoxyethylhydrazine in isopropanol. The reaction temperature rose to 50° C. After completion of the initial reaction, the reaction mixture was heated for 3 hours under reflux.

The reaction product crystallized overnight from the oil left after concentrating the solution. It was recrystallized from a little ethanol.

Melting point: 85°-87° C

Yield: 12 g (43.2% of theory).

Table 4

| Example No. | Structural formula | Recrystallization from | Yield | Melting point, °C |
|---|---|---|---|---|
| 13 | ![F3C structure] | Toluene/ether | 55% of theory | 88-90 |
| 14 | ![CH3 structure] | Methanol | 77% of theory | 149-151 |

EXAMPLE 15

3-ethyl-1-(α-methylbenzyl)-pyrazol-5-one

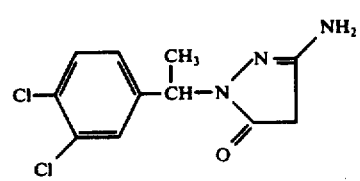

16.5 g of α-methylbenzylhydrazine were dissolved in about 30 ml of dioxane and the solution was added under nitrogen to a solution of 17.5 g of propionylacetoacetic acid ester in dioxane, in the course of which the reaction mixture became warm. After heating for 4 hours under reflux, the reaction mixture was concentrated. The product crystallized out on rubbing. It was recrystallized from methanol.

Melting point: 114°-116° C

Yield: 9.5 g (60% of theory).

EXAMPLE 17

3-amino-1-(α-methyl-3,4-dichlorobenzyl)-pyrazol-5-one 41 g of α-methyl-3,4dichlorobenzylhydrazine, dissolved in absolute ethanol, were added dropwise under nitrogen gas to a solution of 31.8 g of β-amino-β-ethoxyacrylic acid ethyl ester and 1.5 g of p-toluenesulphonic acid in 150 ml of ethanol, at room temperature. After stirring for two hours and leaving to stand overnight, the reaction solution was concentrated to the maximum extent on a rotary evaporator. The residue which remained was dissolved in 2 N sodium hydroxide solution. Any unreacted starting products or by-products were extracted with ether.

The aqueous phase was subsequently brought to pH 5 with acetic acid. The oil hereupon produced was taken up in methylene chloride and the organic phase was dried over $Na_2SO_4$. After evaporation of the solvent, the reaction product crystallized out.

It was recrystallized from methanol.
Melting point: 127°–129° C
Yield: 21 g (38.5% of theory).

In a manner analogous to that described in Example 17, the compounds set forth in Table 5 may be similarly obtained.

20.4 g of phenethylhydrazine were added under nitrogen to 23.7 g of β-amino-β-ethoxyacrylic acid ethyl ester in 150 ml of tetrahydrofurane after a pinch of p-toluenesulphonic acid had been added.

The reaction mixture was stirred overnight under $N_2$ at 40° C and then concentrated in vacuo. The oily residue was dissolved in a little 2 N sodium hydroxide solution. Any starting materials still present, and by-products, were extracted from the aqueous phase with ether.

The aqueous phase was clarified with charcoal, acidified with acetic acid (pH 5) and thoroughly shaken with methylene chloride. The methylene chloride phase was dried with sodium sulphate and on concentration yielded crystalline product which was recrystallized from ethanol.

Melting point: 162°–164° C

Table 5

| No. | Structural formula | Recrystallization from | Yield | Melting point, °C |
|---|---|---|---|---|
| 17a | (3-chloro-4-methylphenyl)(CH₃)CH-N pyrazolone with NH₂ | Methanol | 28% of theory | 86 – 88 |
| 17b | (4-fluorophenyl)(CH₃)CH-N pyrazolone with NH₂ | Ethanol | 33% of theory | 128 – 130 |
| 18 | phenyl(C₂H₅)CH-N pyrazolone with NH₂ | Ethanol | 38% of theory | 170 – 172 |

EXAMPLE 19

3-amino-1-(β-phenethyl)-pyrazol-5-one

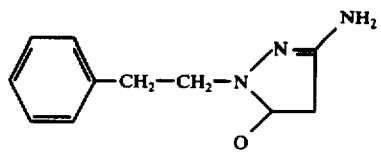

Yield: 14 g (42% of theory).

In a manner analogous to that described in Example 19, the compounds set forth in Table 6 may be similarly obtained.

Table 6

| Example No. | Structural formula | Recrystallization from | Yield | Melting point, °C |
|---|---|---|---|---|
| 20 | F₃C-phenyl-CH₂-CH₂-N pyrazolone NH₂ | Ethanol | 71.5% of theory | 77–79 |
| 21 | Cl-phenyl-CH₂-CH₂-N pyrazolone NH₂ | Ethanol | 65% of theory | 126–128 |
| 22 | CH₃-phenyl-CH₂-CH₂-N pyrazolone NH₂ | Ethanol | 69% of theory | 127–129 |

EXAMPLE 23

3-amino-1-(β-methyl-β-(3-chlorophenoxy)-ethyl)-pyrazol-5-one

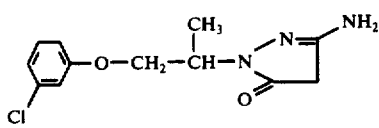

A mixture of 31.8 g of β-amino-β-ethoxyacrylic acid ethyl ester, 150 ml of absolute ethanol, 42 g of β-methyl-β-(3-chlorophenoxy)-ethylhydrazine and a pinch of p-toluene-sulphonic acid was stirred overnight under nitrogen at room temperature and then concentrated in vacuo. The residue was triturated with a little ether. Hereupon, the crude solid crystallized out. It was recrystallized from methanol.

Melting point: 158°–160° C
Yield: 23 g (43% of theory)

In a manner analogous to that described in Example 23, the compounds set forth in Table 7 may be similarly obtained.

What is claimed is:

1. A pharmaceutical composition useful for effecting diuresis and saluresis in humans and animals and for treating hypertension in humans and animals which comprises a diuretic, saluretic or antihypertensive amount of a pyrazol-5-one of the formula:

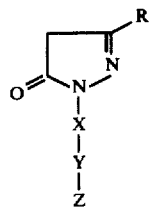

or a pharmaceutically acceptable nontoxic salt thereof wherein

R is hydrogen or lower alkyl;

X is methylene wherein 1 hydrogen atom is substituted by lower alkyl, ethylene, ethylene wherein 1 hydrogen atom on one of the carbon atoms is substituted by lower alkyl or ethylene wherein 1 hydrogen atom on each of the two carbon atoms is substituted by lower alkyl;

Table 7

| Example No. | Structural formula | Recrystallization from | Yield, % of theory | Melting point, °C |
|---|---|---|---|---|
| 24 | | Ethanol | 51 | 130–132 |
| 25 | | Ethanol | 46.5 | 124–126 |
| 26 | | Ethanol | 54 | 91–93 |
| 27 | | Methanol | 44 | 124–126 |
| 28 | | Methanol | 61 | 149–151 |
| 28c | | Methanol | 39 | 133–135 |
| 29 | | Methanol | 55 | 115–117 |
| 30 | | Ethanol | 51 | 100–102 |

Y is a direct bond; and

Z is aryl of 6 to 10 carbon atoms unsubstituted or substituted by:
  a. 1 or 2 of the same or different substituents selected from the group consisting of halogen, trifluoromethyl, alkyl of 1 to 4 carbon atoms, alkenyl of 2 to 4 carbon atoms, alkoxy of 1 to 4 carbon atoms, and alkenoxy of 2 to 4 carbon atoms;
  b. cycloalkyl of 5, 6 and 7 carbon atoms, or cycloalkenyl of 5, 6 or 7 carbon atoms;
  c. nitro;
  d. nitro, and 1 or 2 substituents selected from the group consisting of alkyl of 1 to 4 carbon atoms, alkenyl of 2 to 4 carbon atoms, alkoxy of 1 to 4 carbon atoms, alkenoxy of 2 to 4 carbon atoms, halogen and trifluoromethyl; or
  e. a fused, saturated or unsaturated 5-, 6- or 7-membered ring; in combination with a pharmaceutically acceptable nontoxic inert diluent or carrier.

2. A pharmaceutical composition according to claim 1 wherein

R is hydrogen or alkyl of 1 to 4 carbon atoms; and

Z is phenyl or naphthyl unsubstituted or substituted by
  a. 1 or 2 of the same or different substituents selected from the group consisting of halogen, trifluoromethyl, alkyl of 1 to 4 carbon atoms, alkenyl of 2 to 4 carbon atoms, alkoxy of 1 to 4 carbon atoms, and alkenoxy of 2 to 4 carbon atoms;
  b. nitro;
  c. nitro, and 1 or 2 substituents selected from the group consisting of alkyl of 1 to 4 carbon atoms, alkenyl of 2 to 4 carbon atoms, alkoxy of 1 to 4 carbon atoms, alkenoxy of 2 to 4 carbon atoms, halogen and trifluoromethyl; or
  d. a fused, saturated or unsaturated 5-, 6- or 7-membered ring.

3. A pharmaceutical composition according to claim 1 wherein

R is hydrogen or alkyl of 1 to 4 carbon atoms;

X is methylene wherein 1 hydrogen atom is substituted by alkyl of 1 to 4 carbon atoms, ethylene wherein 1 hydrogen atom on one of the carbon atoms is substituted by methyl or ethyl or ethylene wherein 1 hydrogen atom on each of the two carbon atoms is substituted by methyl or ethyl; and Z is phenyl or naphthyl substituted by:
  a. 1 or 2 of the same or different substituents selected from the group consisting of alkyl of 1 to 8 carbon atoms, and alkenyl of 2 to 8 carbon atoms;
  b. 1 or 2 of the same or different substituents selected from the group consisting of alkoxy of 1 to 6 carbon atoms, and alkenoxy of 2 to 6 carbon atoms;
  c. cycloalkyl of 5, 6 and 7 carbon atoms, or cycloalkenyl of 5, 6 or 7 carbon atoms;
  d. 1 or 2 trifluoromethyl moieties;
  e. nitro; or
  f. a fused, saturated or unsaturated 5-, 6- or 7-membered ring.

4. A pharmaceutical composition according to claim 1 wherein

R is hydrogen or alkyl of 1 to 4 carbon atoms;

X is methylene wherein 1 hydrogen atom is substituted by alkyl of 1 to 4 carbon atoms, ethylene wherein 1 hydrogen atom on one of the carbon atoms is substituted by methyl or ethyl or ethylene wherein 1 hydrogen atom on each of the two carbon atoms of which is substituted by methyl or ethyl; and Z is phenyl; naphthyl; or phenyl substituted by:
  a. 1 or 2 of the same or different substituents selected from the group consisting of alkyl of 1 to 4 carbon atoms, and alkenyl of 2 to 4 carbon atoms;
  b. 1 or 2 of the same or different substituents selected from the group consisting of alkoxy of 1 to 6 carbon atoms, and alkenoxy of 2 to 6 carbon atoms;
  c. cycloalkyl of 5, 6 or 7 carbon atoms, or cycloalkenyl of 5, 6 or 7 carbon atoms;
  d. 1 or 2 trifluoromethyl moieties;
  e. nitro; or
  f. a fused, saturated or unsaturated 5-, 6-or 7-membered ring.

5. A pharmaceutical composition according to claim 1 wherein

R is hydrogen or alkyl of 1 to 4 carbon atoms;

X is methylene wherein 1 hydrogen atom is substituted by alkyl of 1 to 3 carbon atoms, ethylene, ethylene wherein 1 hydrogen atom on one of the carbon atoms is substituted by alkyl of 1 to 3 carbon atoms, or ethylene wherein 1 hydrogen atom on each of the two carbon atoms is substituted by alkyl of 1 to 3 carbon atoms; and Z is phenyl; naphthyl; or phenyl substituted by:
  a. cyclohexyl;
  b. 1 or 2 of the same or different substituents selected from the group consisting of fluorine, chlorine, bromine, iodine, alkyl of 1 to 4 carbon atoms, alkoxy of 1 to 4 carbon atoms, trifluoromethyl, and nitro; or
  c. a trimethylene or tetramethylene moiety which forms a 5- or 6-membered ring together with two carbon atoms of the phenyl ring.

6. A pharmaceutical composition according to claim 1 wherein

R is hydrogen, methyl, ethyl, n-propyl, isopropyl or n-butyl;

X is methylene 1 hydrogen atom of which is substituted by methyl, ethyl, or n-propyl, ethylene, ethylene wherein 1 hydrogen atom is substituted by methyl, ethyl or n-propyl, or ethylene wherein 1 hydrogen atom on each of the two carbon atoms is substituted by methyl;

and

Z is phenyl; naphthyl; or phenyl substituted by alkyl of 1 to 4 carbon atoms, alkoxy of 1 or 2 carbon atoms, fluorine, chlorine, bromine, iodine, trifluoromethyl, nitro, cyclohexyl, dichlorine, chlorine and bromine, chlorine and fluorine, chlorine and methyl, chlorine and trifluoromethyl, fluorine and methyl, trifluoromethyl and methyl and dimethyl, or by a trimethylene or tetramethylene moiety which forms a 5- or 6-membered ring together with two carbon atoms of the phenyl ring.

7. A pharmaceutical composition according to claim 1 wherein

R is hydrogen, methyl or ethyl;

X is methylene wherein 1 hydrogen atom is substituted by methyl, ethyl, or n-propyl, ethylene, or ethylene wherein 1 hydrogen atom on one of the carbon atoms is substituted by methyl;

and

Z is phenyl; naphthyl; or phenyl substituted by 1 or 2 of the same or different substituents selected from the group consisting of fluorine, chlorine, bromine, methyl, ethyl, and trifluoromethyl.

8. A pharmaceutical composition according to claim 1 wherein

R is methyl or ethyl;

X is methylene wherein 1 hydrogen atom is substituted by methyl, ethyl, or n-propyl, ethylene, or ethylene wherein 1 hydrogen atom on one of the carbon atoms is substituted by methyl; and Z is phenyl; naphthyl; or phenyl substituted by fluorine, chlorine, bromine, methyl, trifluoromethyl, dichlorine, dimethyl, chlorine, and methyl, or methyl and ethyl.

9. The pharmaceutical composition according to claim 1 wherein the pyrazol-5-one is

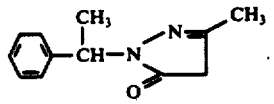

10. The pharmaceutical composition according to claim 1 wherein the pyrazol-5-one is

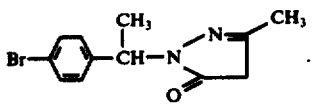

11. The pharmaceutical composition according to claim 1 wherein the pyrazol-5-one is

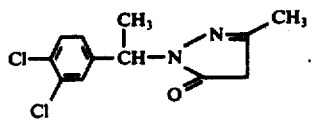

12. The pharmaceutical composition according to claim 1 wherein the pyrazol-5-one is

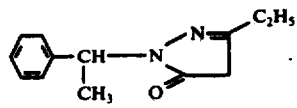

13. A composition according to claim 1 wherein the compound is 3-methyl-1-(α-methyl-3,4-tetramethylenebenzyl)-pyrazol-5-one.

14. A composition according to claim 1 wherein the compound is 3-methyl-1-(α-n-propylbenzyl)-pyrazol-5-one.

15. A composition according to claim 1 wherein the compound is

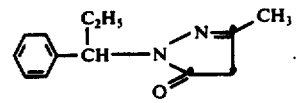

16. A composition according to claim 1 wherein the compound is

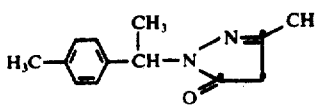

17. A composition according to claim 1 wherein the compound is

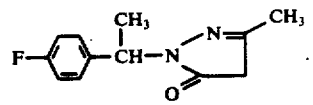

18. A pharmaceutical composition according to claim 1 in oral administration form.

19. A pharmaceutical composition according to claim 1 in parenteral administration form.

20. A pharmaceutical composition according to claim 1 in tablet form.

21. A pharmaceutical composition according to claim 1 in the form of a sterile injectable solution.

22. A method of effecting diuresis and saluresis in humans and animals and for treating hypertension in humans and animals which comprises a diuretic, saluretic or antihypertensive amount of a pyrazol-5-one of the formula:

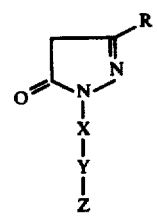

or a pharmaceutically acceptable nontoxic salt thereof wherein

R is hydrogen or lower alkyl;

X is methylene wherein 1 hydrogen atom is substituted by lower alkyl, ethylene, ethylene wherein 1 hydrogen atom on one of the carbon atoms is substituted by lower alkyl or ethylene wherein 1 hydrogen atom on each of the two carbon atoms is substituted by lower alkyl;

Y is a direct bond; and

Z is aryl of 6 to 10 carbon atoms unsubstituted or substituted by:
a. 1 or 2 of the same or different substituents selected from the group consisting of halogen, trifluoromethyl, alkyl of 1 to 4 carbon atoms, alkenyl of 2 to 4 carbon atoms, alkoxy of 1 to 4 carbon atoms, and alkenoxy of 2 to 4 carbon atoms;
b. cycloalkyl of 5, 6 or 7 carbon atoms, or cycloalkenyl of 5, 6 or 7 carbon atoms;
c. nitro;
d. nitro, and 1 or 2 substituents selected from the group consisting of alkyl of 1 to 4 carbon atoms, alkenyl of 2 to 4 carbon atoms, alkoxy of 1 to 4 carbon atoms, alkenoxy of 2 to 4 carbon atoms, halogen and trifluoromethyl; or
e. a fused, saturated or unsaturated 5-, 6- or 7-membered ring;

in combination with a pharmaceutically acceptable nontoxic inert diluent or carrier.

23. A method according to claim 22 wherein

R is hydrogen or alkyl of 1 to 4 carbon atoms; and

Z is phenyl or naphthyl unsubstituted or substituted by
a. 1 or 2 of the same or different substituents selected from the group consisting of halogen, trifluoromethyl, alkyl of 1 to 4 carbon atoms, alkenyl of 2 to 4 carbon atoms, alkoxy of 1 to 4 carbon atoms, and alkenoxy of 2 to 4 carbon atoms;
b. nitro
c. nitro, and 1 or 2 substituents selected from the group consisting of alkyl of 1 to 4 carbon atoms, alkenyl of 2 to 4 carbon atoms, alkoxy of 1 to 4 carbon atoms, alkenoxy of 2 to 4 carbon atoms, halogen and trifluoromethyl; or
d. a fused, saturated or unsaturated 5-, 6- or 7- membered ring.

24. A method according to claim 22 wherein
R is hydrogen or alkyl of 1 to 4 carbon atoms;
X is methylene wherein 1 hydrogen atom is substituted by alkyl of 1 to 4 carbon atoms, ethylene wherein 1 hydrogen atom on one of the carbon atoms is substituted by methyl or ethyl or ethylene wherein 1 hydrogen atom on each of the two carbon atoms is substituted by methyl or ethyl; and
Z is phenyl or naphthyl substituted by:
a. 1 or 2 of the same or different substituents selected from the group consisting of alkyl of 1 to 8 carbon atoms, and alkenyl of 2 to 8 carbon atoms;
b. 1 or 2 of the same or different substituents selected from the group consisting of alkoxy of 1 to 6 carbon atoms, and alkenoxy of 2 to 6 carbon atoms;
c. cycloalkyl of 5, 6 or 7 carbon atoms, or cycloalkenyl of 5, 6 or 7 carbon atoms;
d. 1 or 2 trifluoromethyl moieties;
e. nitro; or
f. a fused, saturated or unsaturated 5-, 6- or 7-membered ring.

25. A method according to claim 22 wherein
R is hydrogen or alkyl of 1 to 4 carbon atoms;
X is methylene wherein 1 hydrogen atom is substituted by alkyl of 1 to 4 carbon atoms, ethylene wherein 1 hydrogen atom on one of the carbon atoms is substituted by methyl or ethyl or ethylene wherein 1 hydrogen atom on each of the two carbon atoms of which is substituted by methyl or ethyl; and
Z is phenyl; naphthyl; or phenyl substituted by:
a. 1 or 2 of the same or different substituents selected from the group consisting of alkyl of 1 to 4 carbon atoms, and alkenyl of 2 to 4 carbon atoms;
b. 1 or 2 of the same or different substituents selected from the group consisting of alkoxy of 1 to 6 carbon atoms, and alkenoxy of 2 to 6 carbon atoms;
c. cycloalkyl of 5, 6 or 7 carbon atoms, or cycloalkenyl of 5, 6 or 7 carbon atoms;
d. 1 or 2 trifluoromethyl moieties;
e. nitro; or
f. a fused, saturated or unsaturated 5-, 6- or 7-membered ring.

26. A method according to claim 22 wherein
R is hydrogen or alkyl of 1 to 4 carbon atoms;
X is methylene wherein 1 hydrogen atom is substituted by alkyl of 1 to 3 carbon atoms, ethylene, ethylene wherein 1 hydrogen atom on one of the carbon atoms is substituted by alkyl of 1 to 3 carbon atoms, or ethylene wherein 1 hydrogen atom on each of the two carbon atoms is substituted by alkyl of 1 to 3 carbon atoms; and
Z is phenyl; naphthyl; or phenyl substituted by: (a) cyclohexyl; (b) 1 or 2 of the same or different substituents selected from the group consisting of fluorine, chlorine, bromine, iodine, alkyl of 1 to 4 carbon atoms, alkoxy of 1 to 4 carbon atoms, trifluoromethyl, and nitro; or
c. a trimethylene or tetramethylene moiety which forms a 5- or 6-membered ring together with two carbon atoms of the phenyl ring.

27. A method according to claim 22 wherein
R is hydrogen, methyl, ethyl, n-propyl, isopropyl or n-butyl;
X is methylene 1 hydrogen atom of which is substituted by methyl, ethyl, or n-propyl, ethylene, ethylene wherein 1 hydrogen atom is substituted by methyl, ethyl or n-propyl, or ethylene wherein 1 hydrogen atom on each of the two carbon atoms is substituted by methyl;
and
Z is phenyl; naphthyl; or phenyl substituted by alkyl of 1 to 4 carbon atoms, alkoxy of 1 or 2 carbon atoms, fluorine, chlorine, bromine, iodine, trifluoromethyl, nitro, cyclohexyl, dichlorine, chlorine and bromine, chlorine and fluorine, chlorine and methyl, chlorine and trifluoromethyl, fluorine and methyl, trifluoromethyl and methyl and dimethyl, or by a trimethylene or tetramethylene moiety which forms a 5- or 6-membered ring together with two carbon atoms of the phenyl ring.

28. A method according to claim 22 wherein
R is hydrogen, methyl or ethyl;
X is methylene wherein 1 hydrogen atom is substituted by methyl, ethyl, or n-propyl, ethylene, or ethylene wherein 1 hydrogen atom on one of the carbon atoms is substituted by methyl;
and
Z is phenyl; naphthyl; or phenyl substituted by 1 or 2 of the same or different substituents selected from the group consisting of fluorine, chlorine, bromine, methyl, ethyl, and trifluoromethyl.

29. A method according to claim 22 wherein
R is methyl or ethyl;
X is methylene wherein 1 hydrogen atom is substituted by methyl, ethyl, or n-propyl, ethylene, or ethylene wherein 1 hydrogen atom on one of the carbon atoms is substituted by methyl;
and
Z is phenyl; naphthyl; or phenyl substituted by fluorine chlorine, bromine, methyl, trifluoromethyl, dichlorine, dimethyl, chlorine and methyl, or methyl and ethyl.

30. The method according to claim 22 wherein the compound is

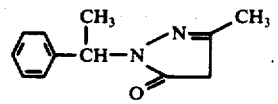

31. The method according to claim 22 wherein the compound is

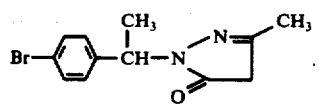

32. The method according to claim 22 wherein the compound is

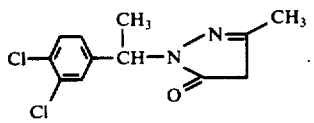

33. The method according to claim 22 wherein the compound is

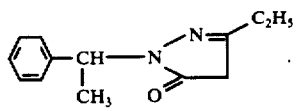

34. A method according to claim 22 wherein the administration is oral.

35. A method according to claim 22 wherein the administration is parenteral.

36. A method according to claim 22 wherein the administration is by tablet.

37. A method according to claim 22 wherein the administration is by sterile, injectable solution.

38. A method according to claim 22 wherein the compound is 3-methyl-1-(α-methyl-3,4-tetramethylenebenzyl)-pyrazol-5-one.

39. A method according to claim 22 wherein the compound is 3-methyl-1-(α-n-propylbenzyl)-pyrazol-5-one.

40. A method according to claim 22 wherein the compound is

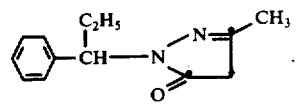

41. A method according to claim 22 wherein the the compound is

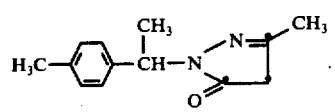

42. A method according to claim 22 wherein the compound is

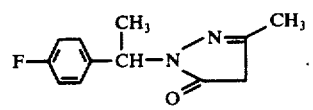

* * * * *